Dec. 7, 1965 L. LENS Plant Pat. 2,579
ROSE PLANT
Filed Oct. 2, 1964
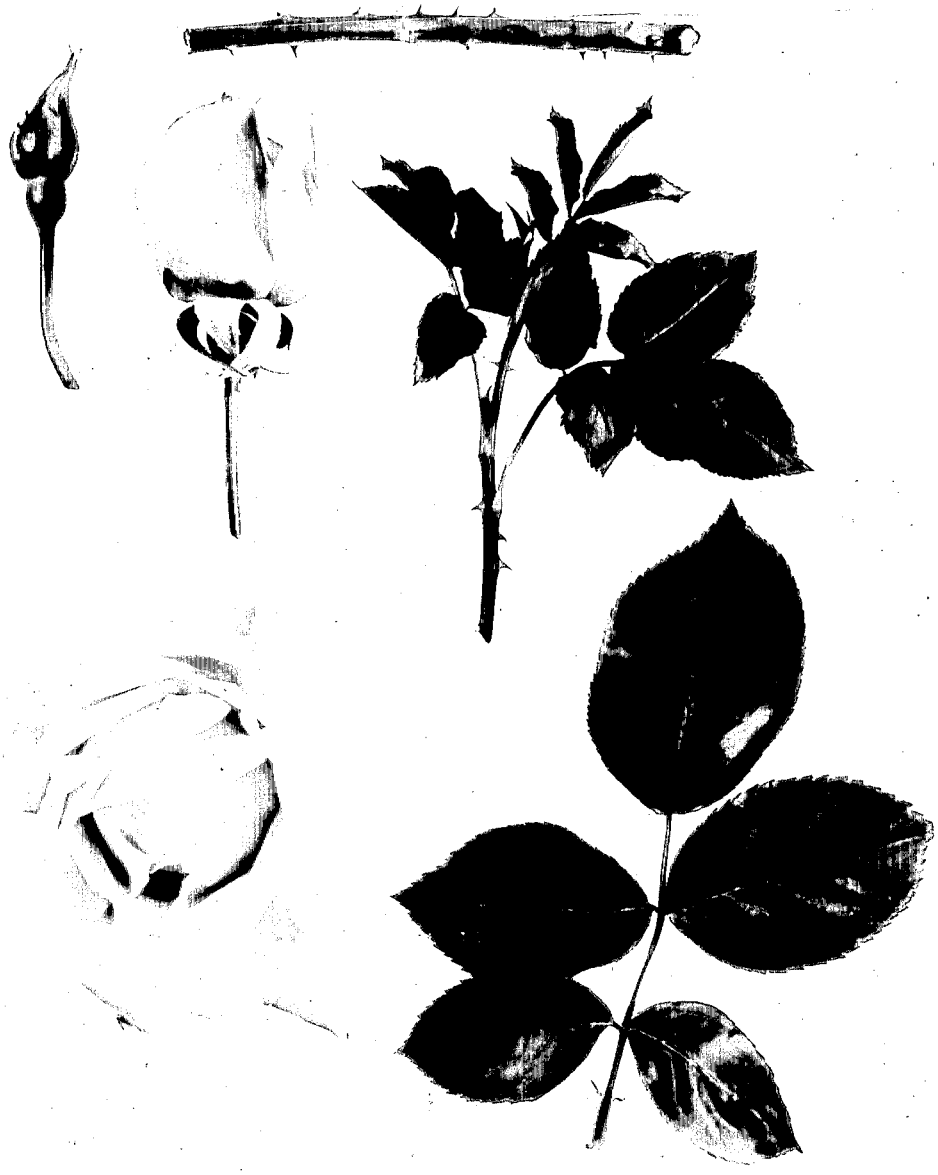
Inventor.
Louis Lens
By: Robb & Robb
Attorneys.

United States Patent Office

Plant Pat. 2,579
Patented Dec. 7, 1965

2,579
ROSE PLANT

Louis Lens, Wavre-Notre-Dame, Belgium, assignor to Jackson & Perkins Company, Newark, N.Y., a corporation of New York Filed Oct. 2, 1964, Ser. No. 401,282
1 Claim. (Cl. Plt.—19)

The present invention relates to a new and distinct variety of rose plant of the hybrid tea class, which was originated by me by crossing an unnamed and unpatented seedling of the variety "Independence" (U.S. Plant Patent No. 1,036) × "Papillon Rose" (unpatented) with another unnamed and unpatented seedling of "Charlotte Armstrong" (U.S. Plant Patent No. 455) × "Floradora" (unpatented).

The primary objective of this breeding was to produce a new rose variety of the hybrid tea class having the good characteristics of the unnamed seedling parents dominated by their antecedents "Independence" and "Charlotte Armstrong," while at the same time bearing flowers of a new color shade. This objective was fully achieved, along with other desirable improvements, as evidenced by the following unique combination of features which are outstanding therein and which distinguish the new variety from its parents, as well as from all other varieties of which I am aware:

(1) A vigorous and upright habit of plant growth;

(2) Great freedom of bloom which continues throughout the summer season;

(3) A distinctive and attractive bud coloration in which the inside of the bud petals are Spinel Red, very lightly overcast with Rose Red, and the reverse of the bud petals are Rose Red, very lightly overcast with Tyrian Rose; and (4) A distinctive and attractive color tonality of the open flowers in which the inside of the flower petals are Eosine Pink, lightly overcast with Begonia Rose, and the reverse of the petals are Eosine Pink, very lightly overcast with Deep Rose Pink, presenting a general color tonality of Rose Doree, very lightly overcast with Eosine Pink.

Asexual reproduction of my new variety as performed by budding at Newark, New York, and Pleasanton, California, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Independence" × "Papillon Rose."

*Pollen parent.*—An unnamed seedling of "Charlotte Armstrong" × "Floradora."

Classification:

*Botanic.*—Hybrid tea.

*Commercial.*—Hybrid tea.

*Flower*

(Observations made from specimens grown outdoors at Newark, New York, U.S.A., in mid-morning, during the latter part of the month of June.)

Blooming habit:

Recurrent—continuous; very free.

Bud:

*Size.*—Large.

*Form.*—Pointed; is not affected by wet or hot weather.

*Color.*—When sepals first divide—Amaranth Purple, Plate 12. When petals begin to unfurl—Amaranth Purple, Plate 12, very lightly overcast with Rose Red, Plate 12. When half-blown: inside of petals —Spinel Red, Plate 26, very lightly overcast with Rose Red, Plate 12; reverse of petals—Rose Red, Plate 12, very lightly overcast with Tyrian Rose, Plate 12.

*Sepals.*—Branched; curl back when petals begin to unfurl. Color: inside—Absinthe Green, Plate 31; outside—Light Bice Green, Plate 17, very lightly overcast in the center with Oxblood Red, Plate 1.

*Calyx.*—Color—Light Bice Green, Plate 17. Shape —pear. Size—large. Aspect—smooth. Odor when rubbed—none.

*Peduncle.* — Length — long. Aspect — prickly. Strength — erect; slender. Color — Light Bice Green, Plate 17.

*Opening.*—Opens up well; is not affected by adverse wether conditions.

Bloom:

*Size.*—Large. Average size when fully expanded—5½ inches.

*Flowers borne.*—Both singly and several together.

*Stems.*—Long; strong.

*Form (when first open).*—Cupped. Permanence—retains its form to the end but outer petals curl back.

*Petalage.*—Double (full but open center). Number of petals under normal conditions—from 25 to 30.

*Color.*—Center of flower—Rose Doree, Plate 1, very lightly overcast with Eosine Pink, Plate 1. Outer petals—Eosine Pink, Plate 1. Base of petals (aiglet)—Maize Yellow, Plate 4. Inside of petal —Eosine Pink, Plate 1, lightly overcast with Begonia Rose, Plate 1. Reverse of petals—Eosine Pink, Plate 1, very lightly overcast with Deep Rose Pink, Plate 12. General tonality from a distance—Rose Doree, Plate 1, very lightly overcast with Eosine Pink, Plate 1.

*Discoloration.*—General tonality at end of first day —Eosine Pink, Plate 1, lightly overcast with Begonia Rose, Plate 1. Second day—Eosine Pink, Plate 1, lightly overcast with Begonia Rose, Plate 1. Third day—Eosine Pink, Plate 1, very lightly overcast with Begonia Rose, Plate 1.

Petals:

*Texture.*—Leathery; is not affected by wet or hot weather.

*Appearance.*—Inside—satiny. Outside—shiny.

*Form.*—Oval; slightly notched.

*Arrangement.* — Imbricated (regularly arranged shingle-like).

*Petaloids in center.*—Few; large.

*Persistence.*—Drop off cleanly.

*Fragrance.*—Moderate. Nature—tea (average hybrid tea scent).

*Lasting quality.*—On the plant—long. As cut flower —long.

*Genital organs*

Stamens, anthers: Medium size; many; regularly arranged around styles. Color—Pinkish Buff, Plate 29.

Stamens, filaments (threads): Long. Color—Napththalene Yellow, Plate 16.

Pollen: Color—Pale Pinkish Buff, Plate 29.

Styles: Loosely separated; uneven length; short; thin.

Stigmas: Color—Colonial Buff, Plate 30.

Ovaries: All enclosed in calyx.

Hips: None.
Seeds: None.

*Plant*

Form: Bush.

Growth: Vigorous; upright.
Foliage: Compound of 3 to 5 leaflets.
*Size.*—Large.
*Quantity.*—Normal.
*Color.*—New foliage: upper side—Bordeaux, Plate 12, very lightly overcast with Yellowish Oil Green, Plate 5 in the center of the leaf; under side—Yellowish Oil Green, Plate 5, lightly overcast with Garnet Brown, Plate 1. Old foilage: upper side—Varley's Green, Plate 18; underside—Courge Green, Plate 17.
*Shape.*—Oval pointed.
*Texture.*—Upper side—leathery and glossy. Under side-smooth.
*Ribs and veins.*—Ordinary.
*Edge.*—Serrated (sawtoothed).
*Serration.*—Both double and single; large.
*Leaf stem.*—Color—Jade Green, Plate 31. Under side—smooth.
*Stipules.*—Medium length; smooth.

Wood:
*New wood.*—Color—Lettuce Green, Plate 5, lightly overcast with Bay, Plate 2. Bark—smooth.
*Old wood.*—Color—Cress Green, Plate 31. Bark—smooth.

Thorns:

*Thorns.*—Quantity: on main stalks from base—few; on laterals from stalk—few. Form—narrow base; medium length; hooked downward. Color (when young)—Acajou Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous and upright habit of plant growth, great freedom of bloom which continues throughout the summer season, a distinctive and attractive bud coloration in which the inside of the bud petals are Spinel Red, very lightly overcast with Rose Red, and the reverse of the bud petals are Rose Red, very lightly overcast with Tyrian Rose, and a distinctive and attractive color tonality of the open flowers in which the inside of the flower petals are Eosine Pink, lightly overcast with Begonia Rose, and the reverse of the petals are Eosine Pink, very lightly overcast with Deep Rose Pink, presenting a general color tonality of Rose Doree, very lightly overcast with Eosine Pink.

No references cited.

ABRAHAM G. STONE, *Primary Examiner.*